United States Patent
Rothfuss et al.

(10) Patent No.: US 11,272,840 B2
(45) Date of Patent: Mar. 15, 2022

(54) TOUCH PROBE PASSIVELY POWERED WIRELESS STENT ANTENNA FOR IMPLANTED SENSOR POWERING AND INTERROGATION

(71) Applicant: UNIVERSITY OF PITTSBURGH—OF THE COMMONWEALTH SYSTEM OF HIGHER EDUCATION, Pittsburgh, PA (US)

(72) Inventors: Michael A. Rothfuss, Pittsburgh, PA (US); Ervin Sejdic, Pittsburgh, PA (US); Michael L. Gimbel, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 562 days.

(21) Appl. No.: 16/096,324

(22) PCT Filed: May 5, 2017

(86) PCT No.: PCT/US2017/031237
§ 371 (c)(1),
(2) Date: Oct. 25, 2018

(87) PCT Pub. No.: WO2017/200769
PCT Pub. Date: Nov. 23, 2017

(65) Prior Publication Data
US 2019/0125189 A1    May 2, 2019

Related U.S. Application Data

(60) Provisional application No. 62/336,897, filed on May 16, 2016.

(51) Int. Cl.
*A61B 5/00* (2006.01)
*H02J 50/20* (2016.01)
(Continued)

(52) U.S. Cl.
CPC ............ *A61B 5/0031* (2013.01); *A61B 5/026* (2013.01); *A61B 5/0215* (2013.01);
(Continued)

(58) Field of Classification Search
CPC ... A61B 5/0031; A61B 5/0215; A61B 5/6862; A61B 2560/0219; A61F 2/07; A61F 2/82
See application file for complete search history.

(56) References Cited

U.S. PATENT DOCUMENTS

| | | | | |
|---|---|---|---|---|
| 4,114,606 A | * | 9/1978 | Seylar | A61B 5/031 600/409 |
| 6,585,763 B1 | * | 7/2003 | Keilman | A61B 8/06 623/1.42 |

(Continued)

*Primary Examiner* — Daniel L Cerioni
*Assistant Examiner* — Raymond P Dulman
(74) *Attorney, Agent, or Firm* — Philip E. Levy; Eckert Seamans Cherin & Mellott, LLC

(57) ABSTRACT

A system and method for wirelessly and passively powering and/or interrogating an implanted stent using a touch probe assembly through a near-field electrical connection not over an air interface. The stent apparatus includes at least one stent member functioning as an antenna and an electronics module coupled to the at least one stent member. Also, a wirelessly and passively powered power meter for use with implanted stents. The power meter includes an electronics module coupled to a stent member, wherein the electronics module includes a programmable oscillator structured to generate an oscillating signal that is proportional to an amount of AC power received by the implantable stent apparatus power meter through the stent member.

5 Claims, 1 Drawing Sheet

(51) Int. Cl.
*A61B 5/0215* (2006.01)
*A61B 5/026* (2006.01)
*A61F 2/82* (2013.01)

(52) U.S. Cl.
CPC ............ *A61B 5/6862* (2013.01); *H02J 50/20* (2016.02); *A61B 2560/0219* (2013.01); *A61F 2/82* (2013.01)

(56) References Cited

U.S. PATENT DOCUMENTS

| | | | |
|---|---|---|---|
| 8,308,794 B2 | 11/2012 | Martinson et al. | |
| 2003/0105388 A1* | 6/2003 | Roy | A61B 5/6876 600/300 |
| 2005/0149170 A1* | 7/2005 | Tassel | A61B 5/028 623/1.15 |
| 2005/0187590 A1* | 8/2005 | Boveja | A61N 1/36082 607/45 |
| 2007/0112344 A1* | 5/2007 | Keilman | A61M 37/0092 606/41 |
| 2009/0043183 A1 | 2/2009 | Kermani et al. | |
| 2009/0157145 A1* | 6/2009 | Cauller | A61N 1/37205 607/60 |
| 2010/0037902 A1* | 2/2010 | Wirtz | A61B 5/07 128/899 |
| 2011/0021887 A1* | 1/2011 | Crivelli | G01D 18/008 600/302 |
| 2011/0282175 A1* | 11/2011 | Geissler | A61B 5/0031 600/365 |
| 2011/0307034 A1* | 12/2011 | Hastings | A61B 18/1492 607/61 |
| 2012/0008714 A1 | 1/2012 | Rizwan | |
| 2013/0018438 A1 | 1/2013 | Chow | |
| 2013/0053711 A1* | 2/2013 | Kotlanka | G01F 1/28 600/505 |
| 2013/0085350 A1* | 4/2013 | Schugt | A61B 5/0031 600/302 |
| 2014/0222110 A1 | 8/2014 | Kibler et al. | |

* cited by examiner

TOUCH PROBE PASSIVELY POWERED WIRELESS STENT ANTENNA FOR IMPLANTED SENSOR POWERING AND INTERROGATION

CROSS-REFERENCE TO RELATED APPLICATIONS

This application is a U.S. National Stage Application under 35 U.S.C. § 371 of International Application No. PCT/US2017/031237, entitled "Touch Probe Passively Powered Wireless Stent Antenna for Implanted Sensor Powering and Interrogation," filed on May 5, 2017, which claims priority under 35 U.S.C. § 119(e) from U.S. provisional patent application No. 62/336,897, entitled "Touch Probe Passively Powered Wireless Stent Antenna for Implanted Sensor Powering and Interrogation," filed on May 16, 2016, the contents of which are incorporated herein by reference.

BACKGROUND OF THE INVENTION

1. Field of the Invention

The present invention pertains to stents that are placed inside a blood vessel, canal, or duct of a patient to aid healing or relieve an obstruction, and in particular, to a system and method for wirelessly and passively powering and/or interrogating an implanted stent using a touch probe assembly. The present invention also pertains to a wirelessly and passively powered power meter for use with implanted stents.

2. Description of the Related Art

Atherosclerosis is a disease described by the accumulation of plaque in arterial walls. This plaque build-up results in narrowing of the arteries. The disease leads to diminished blood flow through the artery and in some cases total loss of flow. Depending on the location of the diseased artery, obstruction of flow limits or eliminates the blood supply to organs, limbs, or other parts of the body. Heart attack, stroke, limb amputation, and even death are possibilities stemming from atherosclerosis.

Atherosclerosis affecting arteries in the lower-limbs is called Peripheral Artery Disease (PAD). PAD is often asymptomatic. Upwards of 80% of sufferers do not show symptoms. Based on patient medical history or symptoms, one of several methods may be employed to detect PAD. These methods include the ankle-brachial index, pulse volume recording, and duplex imaging studies using vascular ultrasound, all of which are non-invasive. If a severe blockage is detected (i.e., stenosis), surgical intervention involving balloon dilation angioplasty of the inner arterial lumen or placement of a medical device called a stent is needed to reintroduce blood flow through the diseased locations. Despite the surgical intervention, the likelihood of restenosis (i.e., re-narrowing of the inner arterial lumen due continued build-up of atheromatous plaque) is high, thereby requiring the patient to comply with quarterly or biannual hospital visits to detect blockages, which may be expensive, such as in the case of duplex studies.

A stent is a hollow mesh tube deployed at the diseased location of an artery to maintain inner lumen diameter for unobstructed blood flow. The stent starts as a collapsed mesh tube, which is then deployed using an angioplasty balloon, causing it to expand and press outwards on the inner lumen. Compared with only angioplasty balloon treatment of a diseased vessel, atherosclerotic arteries in the torso (i.e., coronary arteries, iliac arteries, etc.) have benefited greatly from revascularization with stents. The prevalence of stents in the torso has led to the development of many smart stents, which wirelessly (i.e., via far field telemetry) report the degree of restenosis, precluding the need for patient hospital visits, potentially giving rise to patient compliance and saving costs to hospitals and third party insurers.

SUMMARY OF THE INVENTION

In one embodiment, a method of powering a stent apparatus implanted in the body of a patient is provided, wherein the stent apparatus includes at least one stent member functioning as an antenna and an electronics module coupled to the at least one stent member. The method includes generating an RF signal using a reader device having a touch probe, providing the RF signal to the electronics module of the stent apparatus through a near-field electrical connection not over an air interface between the touch probe and the at least one stent member, converting the RF signal provided to the electronics module to DC power, and using the DC power to power the electronics module.

In another embodiment, a system for powering an implantable device is provided. The system a stent apparatus structured to be implanted in the body of a patient, wherein the stent apparatus includes at least one stent member functioning as an antenna and an electronics module coupled to the at least one stent member. The electronics module includes energy harvesting circuitry. The system further includes a reader device having a touch probe. The reader device is structured to generate an RF signal and provide the RF signal to the electronics module of the stent apparatus through a near-field electrical connection not over an air interface between the touch probe and the at least one stent member. The energy harvesting circuitry is structured to convert the RF signal provided to the electronics module to DC power, and the electronics module is structured to be powered by the DC power.

In still another embodiment, a method of interrogating a stent apparatus implanted in the body of a patient is provided, wherein the stent apparatus includes at least one stent member functioning as an antenna and an electronics module coupled to the at least one stent member. The method includes generating an RF signal using a reader device having a touch probe, providing the RF signal to the electronics module of the stent apparatus through a near-field electrical connection not over an air interface between the touch probe and the at least one stent member, and, in response to the RF interrogation signal being provided to the electronics module, receiving information from the electronics module in the reader device through the near-field electrical connection between the touch probe and the at least one stent member.

In yet another embodiment, a system for interrogating an implantable device is provided. The system includes a stent apparatus structured to be implanted in the body of a patient, wherein the stent apparatus includes at least one stent member functioning as an antenna and an electronics module coupled to the at least one stent member. The system further includes a reader device having a touch probe, the reader device being structured to generate an RF signal and provide the RF signal to the electronics module of the stent apparatus through a near-field electrical connection not over an air interface between the touch probe and the at least one stent member. The electronics module is structured to, in response to the RF signal, cause information to be provided to the reader device through the near-field electrical connection between the touch probe and the at least one stent member.

In still another embodiment, an implantable stent apparatus power meter is provided that includes at least one stent member structured to be implanted in a patient and structured to function as an antenna, and an electronics module coupled to the at least one stent member. The electronics module includes a programmable oscillator, wherein the programmable oscillator is structured to generate an oscillating signal that is proportional to an amount of AC power received by the implantable stent apparatus power meter through the at least one stent member, and wherein the electronics module is structured to cause information based on the oscillating signal to be communicated from the implantable stent apparatus using the at least one stent member.

In still a further embodiment, a system for regulating AC power provided to an implantable device is provided. The system includes an antenna and an electronics module forming a part of the implantable device, wherein the antenna is coupled to the electronics module and is structured to receive the AC power. The electronics module includes a programmable oscillator, wherein the programmable oscillator is structured to generate an oscillating signal that is proportional to a magnitude of the AC power received by the implantable device through the antenna, and wherein the electronics module is structured to cause information based on the oscillating signal to be communicated from the implantable device using the antenna. The system further includes a reader device structured to generate the AC power and receive the information from the implantable device, wherein the reader device implements a control loop configured to adjust the magnitude of the AC power based on the information.

In another embodiment, a method for regulating AC power provided to an implantable device is provided. The method includes generating the AC power in a reader device, transmitting the AC power from the reader device and causing the AC power to be received in the implantable device, wherein in response to receiving the AC power the implantable device generates an oscillating signal that is proportional to a magnitude of the AC power received by the implantable device, and receiving information based on the oscillating signal in the reader device and adjusting the magnitude of the AC power based on the information.

In yet a further embodiment, an RE reader device is provided that includes a radio component structured to generate and transmit an AC signal to an implantable device, wherein in response to receiving the AC signal the implantable device generates an oscillating signal that is proportional to a magnitude of the AC signal received by the implantable device wherein the radio component is further structured to receive information based on the oscillating signal from the implantable device, and a control system structured adjust the magnitude of the AC signal based on the information.

DETAILED DESCRIPTION OF EXEMPLARY EMBODIMENTS

Figure 1:
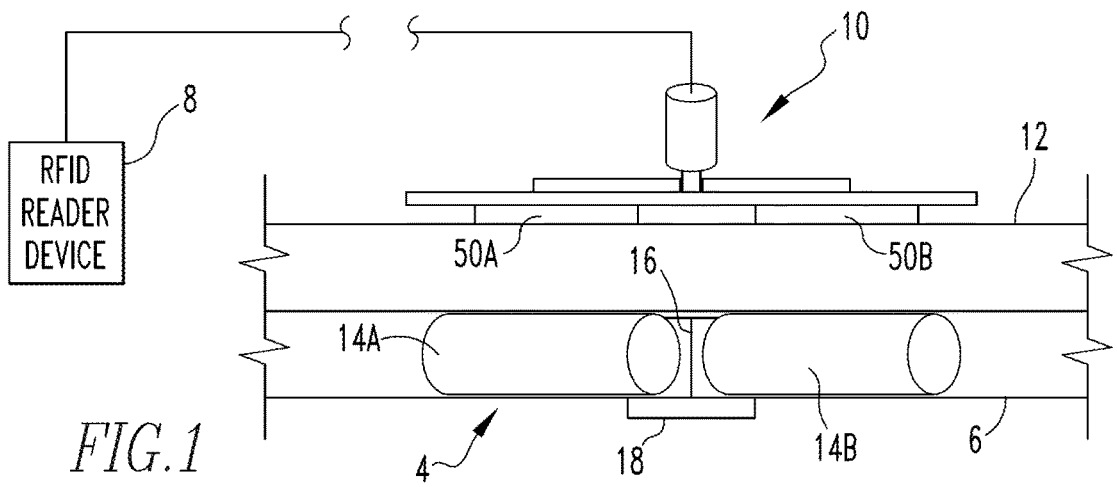
FIG. 1 is a block diagram of a system for wirelessly powering and communicating with a stent apparatus that has been surgically implanted in a blood vessel of a patient according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body.

As used herein, the statement that two or more parts or components "engage" one another shall mean that the parts exert a force against one another either directly or through one or more intermediate parts or components.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term "near-field" shall mean the region that is in proximity to an antenna or another radiating structure where the electric and magnetic fields do not have a plane-wave characteristic but vary greatly from one point to another. Furthermore, the near-field can be subdivided into two regions which are named the reactive near-field and the radiating near-field. The reactive near-field is closest to the radiating antenna and contains almost all of the stored energy, whereas the radiating near-field is that portion of the near-field region between the far-field region and the reactive near-field portion of the near-field region, wherein the angular field distribution is dependent upon the distance from the antenna.

As used herein, the term "far-field" shall mean the region where the electromagnetic field has a plane-wave characteristic, i.e., it has a uniform distribution of the electric and magnetic field strength in planes transverse to the direction of propagation.

As used herein, the term "dipole antenna" shall mean an antenna or another radiating structure having two conductive elements, such as metal wires or rods, which are usually bilaterally symmetrical, wherein each side of a feedline to a transmitter and/or a receiver is connected to one of the two conductive elements and wherein the transmit mode input (i.e., driving current) is applied to and/or the receive mode output is taken from a point between the two conductive elements by the feedline.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

FIG. 1 is a block diagram of a system 2 for wirelessly powering and communicating with a stent apparatus 4 that has been surgically implanted in a blood vessel 6 of the patient (or another part of the body such as a canal or duct) according to an exemplary embodiment of the present invention. As seen in FIG. 1, system 2 includes an RFID reader device 8 including a touch probe device 10. As described in greater detail herein, RFID reader device 8 having touch probe device 10 allows power to be provided to and information to be read from and/or transmitted to stent apparatus 4 through a direct electrical connection (i.e., not over an air interface, but rather transcutaneously) between touch probe device 10 and stent apparatus 4 through skin 12 of patient.

Figure 2:
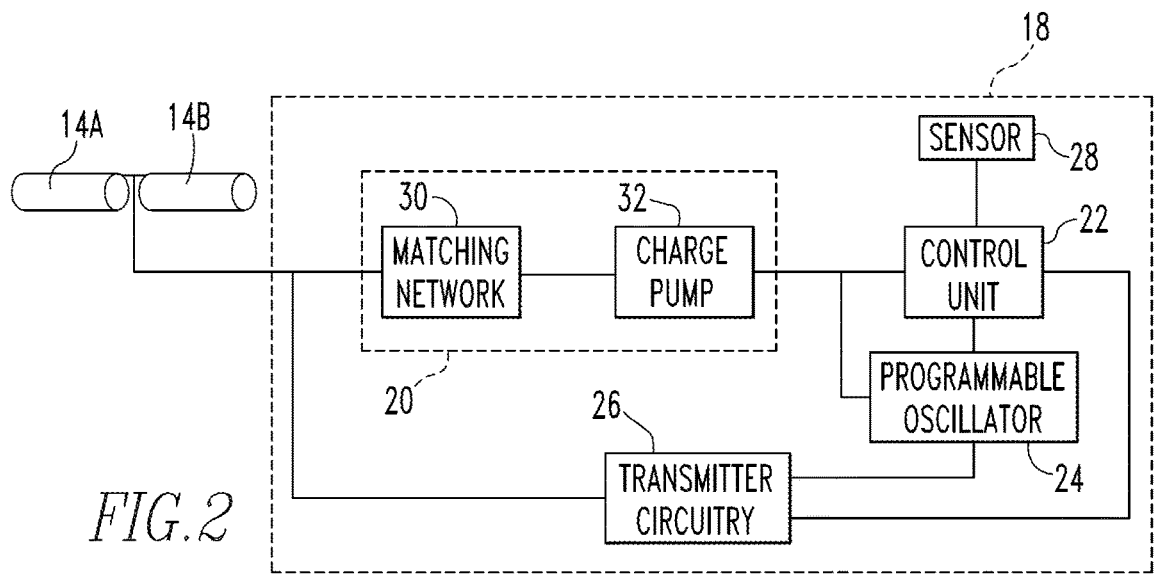
FIG. 2 is a schematic representation of one particular, non-limiting exemplary embodiment of a stent apparatus that may be used to implement the system of FIG. 1.
Figure 3:
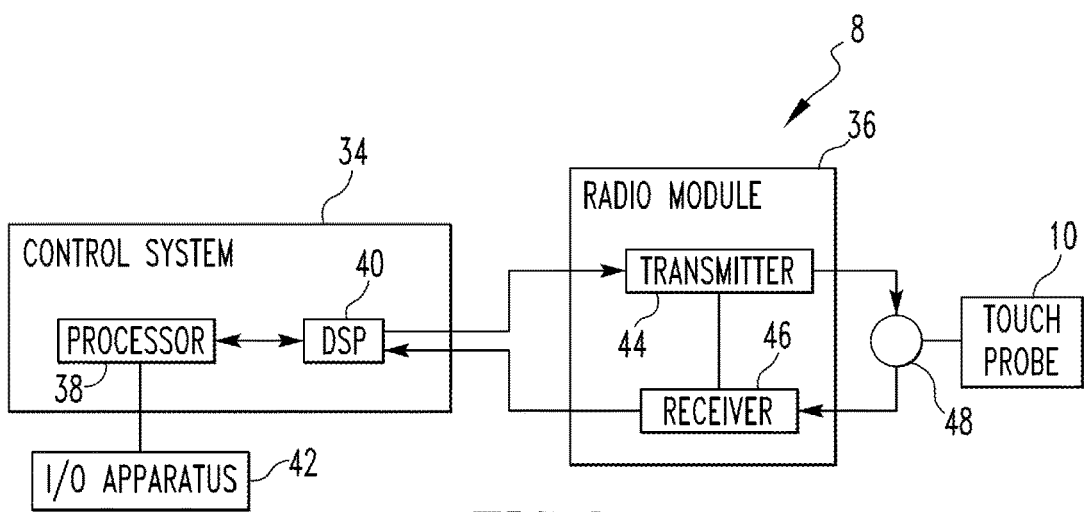
FIG. 3 is a block diagram of one particular exemplary embodiment of an RFID reader device that may be used to implement the system of FIG. 1.

FIG. 2 is a schematic representation of one particular, non-limiting exemplary embodiment of stent apparatus 4 that may be employed to implement system 2. In addition, FIG. 3 is a block diagram of one particular exemplary embodiment of an RFID reader device 8 that may be used to implement system 2 in combination with stent apparatus 4 so that stent apparatus 4 can powered, read from and/or written to by making a direct (i.e., a non-air interface) electrical connection thereto through skin 12. Both stent apparatus 4 and RFID reader device 8 are described in detail below.

As seen in FIG. 1 and FIG. 2, stent apparatus 4 includes a first stent member 14A and a second stent member 14B that are connected to one another by a feedline 16 provided therebetween. Each stent member 14A, 14B is, in the exemplary embodiment, a metal mesh tube. Together, first stent member 14A and second stent member 14B form a dipole antenna that is used to enable power and information signals to be communicated to and from stent apparatus 4 as described herein. Stent apparatus 4 also includes an electronics module 18 (described below) that is operatively connected to first and second stent members 14A and 14B by feedline 16.

Stent apparatus 4 may either be powered from the modulated electromagnetic field provided by RFID reader device 8 (known as a passive device), or may contain its own internal power source, such as a battery (known as an active device).

In the exemplary embodiment, stent apparatus 4 is a passive device powered by an RF signal sent by RFID reader device 8 in the manner described herein. One passive tag technology employed in far-field applications, known as backscatter technology, generates signals by modulating the carrier signal sent from the RFID reader. A similar passive tag technology employed in near-field applications that also generates signals by modulating the carrier signal sent from the RFID reader is known as load modulation. In both the backscattering technique and the load modulation technique, the carrier signal is modulated by modulating (i.e. changing) the load on the antenna at the tag using, for example, shunting circuitry. In another passive technology, described in U.S. Pat. Nos. 6,289,237, 6,615,074, 6,856,291, 7,057,514, and 7,084,605 (and commonly referred to as energy harvesting). RF energy from the RFID reader is harvested and converted to a DC voltage by an antenna/matching circuit/charge pump combination. The DC voltage is then used to power the circuitry that transmits information to the RFID reader at, for example, a different frequency. In the exemplary embodiment described herein, stent apparatus 4 employees a near-field load modulation technique for communicating information to RFID reader device 8.

FIG. 2 is a schematic representation of one particular, non-limiting embodiment of the disclosed concept wherein passive technology in the form of load modulation as just described is employed to power electronics module 18 of stent apparatus 4. As seen in FIG. 2, electronics module 18 of the present embodiment includes energy harvesting circuitry 20 that is operatively coupled to a control unit 22 and a programmable oscillator 24, which are both operatively coupled to load modulation circuitry 26. A sensor 28, such as a blood flow or blood pressure sensing device, is operably coupled to control unit 22 and is structured to measure one or more parameters relating to the patient which are indicative of the degree of restenosis of the blood vessel 6. Other examples of sensor 28 include optic sensors, chemosensors, electrical charge/field sensors, temperature sensors, accelerometer sensors, Global Positioning Satellite receivers, Oxygen sensors, $CO_2$ sensors, other gas sensor (carbon monoxide, nitrogen, nitric oxide, anesthetic gas, etc.), blood sugar sensors, other blood chemistry sensors (lactate, electrolytes, etc), microorganism sensors, antibody/antigen sensors, and DNA/RNA sequence sensors. In operation, and as described in more detail herein, energy harvesting circuitry 20 is structured to receive RF energy from RFID reader device 8 in the near-field and harvest energy therefrom by converting (i.e., rectifying) the received RF energy into DC energy, e.g., a DC voltage. The DC energy is then used to power control unit 22, programmable oscillator 24 and load modulation circuitry 26. Control unit 22 may be, for example, a microprocessor, a microcontroller or some other suitable custom control circuitry, an associated memory, and additional logic circuitry. Load modulation circuitry 26 is structured to modulate the RF carrier signal sent from the RFID reader device 8 in order to communicate information to RFID reader device 8. For example, load modulation circuitry 26 may be caused to modulate the RF carrier signal based on one or more readings from sensor 28 (stored in the memory of control unit 22). RFID reader device 8 is thus able to "observe" the sensor signal based on "load modulation." As another example, described below, load modulation circuitry 26 may be caused to modulate the RF carrier signal based on the output of programmable oscillator 24.

Programmable oscillator 24 is a device which outputs an oscillating signal (e.g., a square wave) wherein the frequency of the oscillating signal is proportional to the amount of DC power that is applied to the device. An example of a suitable programmable oscillator 24 is part number LTC 6906 sold by Linear Technologies. As described in greater detail herein, in one particular exemplary embodiment, programmable oscillator 24 is used to implement a passively powered power meter for measuring the amount of AC power that is being received by stent apparatus 4. It will be appreciated, however, that such a power meter is optional and that electronics module 18 may omit programmable oscillator 24 if such a power meter is not desired.

In the particular embodiment shown in FIG. 2, energy harvesting circuitry 20 of electronics module 18 includes a matching network 30 electrically connected to feedline 16. Matching network 30 is also electrically connected to a voltage boosting and rectifying circuit preferably in the form of a one or more stage charge pump 32. Charge pumps are well known in the art. Basically, one stage of a charge pump increases the effective amplitude of an AC input voltage with the resulting increased DC voltage appearing on an output capacitor. Successive stages of a charge pump, if present, will essentially increase the voltage from the previous stage resulting in an increased output voltage. In operation, first and second stent member 14A and 14B receive RF energy that is transmitted by RFID reader device 8 as described herein. The received RF energy is provided, in the form of an AC signal, to charge pump 32 through the associated matching network 30. Charge pump 32 rectifies the received AC signal to produce a DC signal that is amplified as compared to what it would have been had a simple rectifier been used. In the exemplary embodiment, matching network 30 is chosen (i.e., its impedance is chosen) so as to maximize some criterion such as the voltage of the DC signal output by charge pump 32.

Referring again to FIG. 3, RFID reader device 8 of the present, non-limiting exemplary embodiment will now be described. As noted elsewhere herein and as described in detail below, RFID reader device 8 is able to provide power to, read information from and transmit information to stent apparatus 4 by making a direct (i.e., non-air interface) electrical connection thereto through skin 12 so that the power and information may be transmitted to stent apparatus 4 in the near-field. RFID reader device 8 includes a control system 34 and a radio module 36. In the exemplary embodiment shown in FIG. 3, control system 34 includes a processor 38, such as a microcontroller or microprocessor, and a digital signal processor (DSP) 40, although other configurations are possible. Processor 38 provides control over high level operation of RFID reader device 8 and may communicate with an external network and/or peripheral devices such as, without limitation, I/O apparatus 42 (which enables information to be input into and output from RFID reader device 8). I/O apparatus 42 may include a display, a keyboard, a touchscreen, or some combination thereof. DSP 40 provides direct control over all operations of radio module 36 in response to high level commands provided by processor 38, and processes data signals received from stent apparatus 4 as described herein. Radio module 36 is adapted to provide for communications to/from stent apparatus 4 by generating and receiving RF signals in the manner described herein.

More particularly, radio module 36 further comprises a transmitter portion 44, a receiver portion 46, and a hybrid 48. Hybrid 48 may further comprise a circulator. Transmitter portion 44 preferably includes a local oscillator that generates an RF carrier frequency. Transmitter portion 44 sends a transmission signal modulated by the RF carrier frequency to hybrid 48, which in turn passes the signal to touch probe device 10. Hybrid 48 connects transmitter portion 44 and receiver portion 46 to touch probe device 10 while isolating them from each other. In particular, hybrid 48 allows a relatively strong signal to be sent from transmitter portion 44 while simultaneously receiving a weaker signal sent from stent apparatus 4. Touch probe device 10 includes electrical contacts or electrodes 50A and 50B that are adapted to be selectively and temporarily mated and brought into electrical contact with stent members 14A and 14B, acting as a dipole antenna, of stent apparatus 4 through skin 12. As such, the signals generated by RFID reader device 8 (e.g., an interrogation signal), that would in known RFID readers be sent over an air interface, may instead be directly transmitted to stent apparatus 4, and thus electronics module 18 provided therein, wirelessly (but without an air interface) through the near-field via transcutaneous communication through skin 12. Similarly, the modulated signals generated by electronics module 18 may be directly communicated wirelessly (but not over an air interface) to RFID reader device 8 through touch probe device 10 in the near-field via transcutaneous communication using stent members 14A and 14B, acting as a dipole antenna. Thus, in such a configuration, RFID reader device 8 is able to interrogate stent apparatus 4 by generating an RF interrogation signal and transmitting that signal to stent apparatus 4 in the manner just described. In response, stent apparatus 4 will modulate the RF signal to communicate information, such as information based on the sensor 28, to RFID reader device 8 in the manner just described. In one particular embodiment, touch probe device 10 is wand-like device having two conductors 50A and 50B fixed at the end distal thereof with a center to center distance to accommodate and generally match the spacing of stent members 14A and 14B shown in FIG. 1.

The signals from stent apparatus 4 communicated through touch probe device 10 as just described are passed back to hybrid 48, which forwards the signals to receiver portion 46. Receiver portion 46 mixes the captured signals with the RF carrier frequency generated by the local oscillator to directly downconvert the captured signals to a baseband information signal, which is provided to DSP 40 for processing thereby.

Thus, as just described, system 2 implements a touch probe method for wirelessly (but not over an air interface) powering near-field electronics and sensors connected to a stent implanted within the body. System 2 also implements a touch probe method for wirelessly (but not over an air interface) interrogating near-field electronics and sensors connected to a stent implanted within the body. In such methods, the touch probe confines power within a small area around the implanted device, which stands to reduce the chance of interfering with nearby electronics in the operating room or other implanted electronics such as pacemakers. Additionally, the touch probe methods of powering and interrogating described herein lead to increased security in much the same way near field communication (NFC) systems require near contact between a reader and an interrogated device. As a result, information cannot be mistakenly or purposefully read from a device without deliberate physical access.

As noted elsewhere herein, according to a further embodiment of the disclosed concept, stent apparatus 4 may also be used to implement a wireless, passively powered power meter. One potential use for such an implementation is to have the power meter form part of a control loop that wirelessly reports the amount of power being received by stent apparatus 4 back to RFID reader device 8. RFID reader device 8 may then, as needed, reduce the power output thereby in order to adhere to federal regulations on limitations for power absorbed in tissue, which is called the specific absorption rate (SAR) limit. In particular, in the illustrated embodiment, during operation, programmable oscillator 24 will output an oscillating signal (e.g., a square wave) having a frequency which is proportional to the DC voltage being provided thereto by energy harvesting circuitry 20. Because the DC voltage output by energy harvesting circuitry 20 is proportional to the AC voltage being received through the first and second stent members 14A and 14B, the oscillating signal output by programmable oscillator 24 is also proportional to the amount of AC power being received by stent apparatus 4. That oscillating signal may then be used by load modulation circuitry 26 to communicate information based on and indicative of the oscillating signal to RFID reader 8 through touch probe 10 as described herein to be used by RFID reader 8 in a control loop as just described.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of powering a stent apparatus implanted in a body of a patient, the stent apparatus including at least one stent member functioning as an antenna and an electronics module coupled to the at least one stent member, the method comprising:
    surgically implanting the at least one stent member in a blood vessel forming a natural part of the body of the patient to provide structural support to the blood vessel, the at least one stent member comprising a metal mesh tube;
    generating an RF signal using a reader device having a touch probe;
    providing the RF signal to the electronics module of the stent apparatus through a near-field electrical connection not over an air interface between the touch probe and the at least one stent member; and
    converting the RF signal provided to the electronics module to DC power; and using the DC power to power the electronics module;
    wherein the stent apparatus includes a feedline having a first conductive portion having a first side and a second side opposite the first side and a second conductive portion coupled to the first conductive portion, the second conductive portion being directly coupled to the electronics module, wherein the at least one stent member includes a first stent member comprising a first metal mesh tube directly coupled to the first side of the first conductive portion and a second stent member comprising a second metal mesh tube directly coupled to the second side of the first conductive portion, wherein the feedline, the first metal mesh tube and the second metal mesh tube form a dipole antenna, and wherein the touch probe includes a first electrical contact and a second electrical contact.

2. The method according to claim 1, wherein the electronics module includes a sensor, wherein the method includes communicating information based on an output of the sensor from the stent apparatus to the reader device through the near-field electrical connection between the touch probe and the at least one stent member.

3. A system for powering an implantable device, comprising:
    a stent apparatus including (i) at least one stent member comprising a metal mesh tube, the at least one stent member being configured to be surgically implanted in a blood vessel forming a natural part of a body of a patient to provide structural support to the blood vessel and functioning as an antenna, and (ii) an electronics module coupled to the at least one stent member, the electronics module including energy harvesting circuitry; and
    a reader device having a touch probe, the reader device being structured to generate an RF signal and provide the RF signal to the electronics module of the stent apparatus through a near-field electrical connection not over an air interface between the touch probe and the at least one stent member, wherein the energy harvesting circuitry is structured to convert the RF signal provided to the electronics module to DC power, and wherein the electronics module is structured to be powered by the DC power;
    wherein the stent apparatus includes a feedline having a first conductive portion having a first side and a second side opposite the first side and a second conductive portion coupled to the first conductive portion, the second conductive portion being directly coupled to the electronics module, wherein the at least one stent member includes a first stent member comprising a first metal mesh tube directly coupled to the first side of the first conductive portion and a second stent member comprising a second metal mesh tube directly coupled to the second side of the first conductive portion, wherein the feedline, the first metal mesh tube and the second metal mesh tube form a dipole antenna, and wherein the touch probe includes a first electrical contact and a second electrical contact.

4. The system according to claim 3, wherein the electronics module includes a sensor and load modulation circuitry coupled to the at least one stent member, the load modulation circuitry being structured to modulate the RF signal based on an output of the sensor.

5. The system according to claim 4, wherein the sensor is a blood flow sensor or a blood pressure sensor.

* * * * *